United States Patent [19]

Nomura et al.

[11] Patent Number: 5,843,789
[45] Date of Patent: Dec. 1, 1998

[54] METHOD OF ANALYSIS OF GENOMIC BIOPOLYMER AND POROUS MATERIALS FOR GENOMIC ANALYSES

[75] Inventors: Hiroshi Nomura, Shorewood; Jong Hyung Ahn, Minnetonka, both of Minn.

[73] Assignee: NeoMecs Incorporated, St. Louis Park, Minn.

[21] Appl. No.: 442,170

[22] Filed: May 16, 1995

[51] Int. Cl.$^6$ .............................. G01N 33/53; C12Q 1/00; C08F 2/46; B01D 69/00
[52] U.S. Cl. .................... 436/164; 210/490; 210/500.35; 210/500.38; 422/55; 427/488; 427/491; 435/4; 435/6; 436/172
[58] Field of Search ................................ 422/55, 57, 180; 210/500.35, 500.38, 500.27, 490, 500.42; 264/41, 49; 435/4, 6; 427/488, 491; 436/164, 172

[56] References Cited

U.S. PATENT DOCUMENTS

| | | | |
|---|---|---|---|
| 4,473,474 | 9/1984 | Ostreicher et al. | 210/636 |
| 4,919,811 | 4/1990 | Davis | 210/500.36 |
| 5,019,260 | 5/1991 | Gsell et al. | 210/490 |
| 5,262,451 | 11/1993 | Winters et al. | 523/112 |
| 5,470,307 | 11/1995 | Lindall | 604/20 |

FOREIGN PATENT DOCUMENTS

| | | |
|---|---|---|
| 0249513 | 12/1987 | European Pat. Off. |
| 0294186 | 12/1988 | European Pat. Off. |

OTHER PUBLICATIONS

G.–H. Hsiue and C.–C. Wang, "Functionalization of polyethylene surface using plasma–induced graft copolymerization of acrylic acid," J. Polymer Sci., Part A: Polymer Chem., vol. 31, pp. 3327–3337 (1993).

S. Yuan et al., "Immobilization of high–affinity heparin oligosaccharides to radiofrequency plqwmq–modified polyethylene," J. Biomedical Materials Res., vol. 27, pp. 8811–8819 (1993).

T.–M. Ko and S. Cooper, "Surface properties and platelet adhesions characteristics of acrylic acid and allylamine plasma–treated polyethylene," J. Applied Polymer Sci., vol. 47, pp. 1601–1619 (1993).

M. Muratsugu et al., "Plasma–polymerized allylamine film used as a new solid phase in immunoradiometric assay (IRMA): effect of antibody Fab2 fragment concentration on dose response in two–site IRMA," Chem. Pharm. Bull., vol. 40, pp. 501–503 (1992).

M. Mutatsuqu, S. Kurosawa & N. Kamo, "Adsorption and desorption of anti–hIgG on plasma–polymerized allylamine thin film: the application of the film to immunoassay," J. Colloid Interface Sci., vol. 147, pp. 378–386 (1991).

T.–J. Chu et al., "Low flourescence background electroblotting membrane in DNA sequencing," Electrophoresis, vol. 13, pp. 105–114 (1992).

*Primary Examiner*—John Kim
*Attorney, Agent, or Firm*—Robert J. Petersen

[57] ABSTRACT

Improved porous materials useful in blotting analyses of proteinaceous and genomic matter are prepared by treating porous substrates with a gas plasma containing at least one monomer. Thus, a porous sheet-like substrate is modified by means of a deposit of a plasma polymerizate on at least one of its surfaces, whereby this modified surface exhibits reduced nonspecific binding of chemical probes in a blotting analysis. By means of a controlled deposition of the plasma polymer at a plasma composite parameter W/FM of less than $1.0 \times 10^9$ Joules/kilogram, improved porous materials are obtained having increased signal-to-background ratios and enhanced sensitivities in genomic analyses. In a particularly preferred embodiment, a porous, positively charged nylon membrane is treated with a plasma containing an unsaturated carboxylic acid monomer, whereby the membrane surface is modified with an acidic polymeric deposit, this modification resulting in reduced nonspecific binding of oligonucleotide probes and increased sensitivity in chemiluminescent analyses of polynucleotide sequences.

24 Claims, 2 Drawing Sheets

5,843,789

METHOD OF ANALYSIS OF GENOMIC BIOPOLYMER AND POROUS MATERIALS FOR GENOMIC ANALYSES

ACKNOWLEDGEMENT

This invention was made with government support under Grant No. 1R43 GM47906-01 by the U.S. Department of Health and Human Services, Public Health Service, National Institute of General Medical Sciences, under the Small Business Innovation Research Program.

FIELD OF THE INVENTION

The invention relates to blotting and blot/transfer membranes useful in the analysis of nucleic acids and proteins. More specifically, the invention relates to porous materials having improved surface characteristics for genomic and immunoassay analyses, and to methods for generating these improved materials via surface modification by gas plasma polymerization.

BACKGROUND

In the analyses of proteins and of genomic and mitochondrial nucleic acid biomolecules, one well known approach is to separate mixtures of such biomolecules into a series of bands by gel electrophoresis chromatography. For example, deoxyribonucleic acid (DNA) and ribonucleic acid (RNA) biopolymers are commonly separated electrophoretically in agarose gel media. Proteins are commonly separated electrophoretically in polyacrylamide gel media. Having been separated thus, specific bands of these biopolymers (particularly genomic matter) are often intended to be subjected to hybridization or derivatization procedures to determine the presence and, at times, the quantity of specific components or submolecular sequences. But electrophoresis gel media are unstable environments for derivatization and measurement of targeted submolecular sequences. One technique that has come into widespread usage involves transfer of these bands from electrophoresis gel media onto porous membranes by "transfer blotting." Another well known approach is to apply digests of nucleic acid matter, for example, directly onto porous membranes, such as in the form of dot or slot patterns. This, too, is a blotting technique utilizing porous media. Adsorption of the biopolymers to the porous media stabilizes the biopolymers in place, to which a variety of analysis techniques may then be applied. It is common to additionally fix the biomolecules in place by crosslinking or covalent binding techniques.

The immobilized biopolymers may be subsequently exposed to one or more chemical probes, i. e., probes are hybridized to targeted sequences in the adsorbed biopolymers, if present. Until recently, hybridization agents contained radioisotopes. Specific biomolecules or biomolecular sequences were detected visually by radiometric development of images on photographic films placed in contact with the media containing the immobilized, derivatized biomolecules. Radioimmunoassay methods have now been supplemented with new, nonradiometric approaches including chemiluminescent, fluorescent and calorimeter methods of detection, or with polymerase chain reaction (PCR) methods of greatly amplifying specific nucleic acid sequences, or with combinations of these techniques. The chemiluminescent, fluorescent and colorimetric methods of detection have not profoundly displaced radioimmunoassay methods, despite environmental and regulatory concerns about the handling of radioactive chemicals. A drawback limiting the full scale adoption of these newer methods is been their generally lower level of sensitivity versus radioimmunoassay sensitivity.

The porous membranes are chosen, in part, for affinity of specific biopolymers to their surfaces and, in part, for their loading capacity for such biopolymers. Thus, porous nitrocellulose membranes have been particularly useful as blotting media for proteinaceous biopolymers. Porous polyamide ("nylon") membranes have come into wide use as blotting media for receiving DNA and RNA biopolymers. The latter biopolymers exhibit far greater hydrophobic adsorption characteristics than proteinaceous biopolymers, and adsorb more fully to porous nylon media than to nitrocellulose media. Porous nylon materials suitable for dot, slot or transfer blot techniques were originally already available in the form of, and intended for use as, microfiltration membranes. Tailoring of these microfiltration membranes for blot analyses has commonly entailed building into their surfaces increased cationic character. Positively charged polyamide membranes often exhibit even better binding and loading capacity for these genomic biopolymers than do the neutral polyamide media.

During hybridization of chemical probes to targeted submolecular sequences in the proteinaceous or genomic materials immobilized on porous media, adsorption of the chemical probes to the porous substrates occurs as well. For example, a porous nylon membrane having a favorable affinity for a DNA biomolecule will naturally also exhibit an appreciable affinity for a probe containing an oligomeric DNA sequence that will hybridize to a corresponding target sequence in the immobilized DNA. The probes, being very closely related chemically to the targets, will naturally show similar adsorption affinities. A persistent problem with porous materials used in these methods, therefore, is high nonspecific binding of most types of probes, whether used in radiometric, colorimetric, chemiluminescent, or fluorescent analyses. Tailoring of membranes to have cationic character has not ameliorated this drawback. The problem of high nonspecific binding is particularly present in the newer methods of analysis (colorimetric, chemiluminescent, fluorescent). This results in an unsatisfactorily low signal-to-background ratio as compared to radioimmunoassay, and a high background that most users find to be detrimental.

Thus, a need exists for porous materials that have an improved signal-to-background ratio (i.e., signal-to-noise ratio) and low overall backgrounds, particularly in the analysis of genomic matter. That is, porous materials are needed that retain favorably high levels of loading and binding toward proteins and nucleic acid samples, particularly the latter, while exhibiting little or no nonspecific binding by probes being hybridized to targeted sequences in those biopglymers.

An object of the present invention, therefore, is the preparation of a porous material having a favorably high binding capacity toward biomatter, while exhibiting lowered levels of nonspecific binding by probes specific to the biomatter.

It is a further object of the invention to provide porous materials that exhibit a high signal-to-noise ratio in the analysis of nucleic acid biomatter, whether by radioimmunoassay, chemiluminescent, fluorescent or colorimetric probing techniques.

It is a further object of the invention to exploit the differences, albeit small, in binding characteristics of chemical probes vis-a-vis the targeted biomatter to achieve improved signal-to-noise ratios.

It is a further object of the invention to provide improved porous materials of this nature without loss of desirable physical strength and handling characteristics associated with presently used porous materials.

Additional objects, advantages and novel features of the invention will be set forth in the description of the invention which follows, or in part will become apparent to those skilled in the art upon review of the following description or as may be learned through practice of the invention.

SUMMARY OF THE INVENTION

Improved porous materials have now been developed whereby improved detection of specific biomolecules and submolecular chemical sequences in biomolecules may be obtained in proteinaceous and genomic analysis procedures. More specifically, improved porous media have now been developed and are disclosed herein, whereby background adsorption of chemical probes is reduced favorably relative to hybridized levels of the same probes with targeted biomolecular sequences in biopolymers immobilized on these media. One embodiment of the invention resides in these improved porous media and is disclosed herein. Another embodiment of the invention resides in the method of making these improved porous media, which method is also disclosed herein. Another embodiment of the invention resides in the use of these improved materials in genomic and immunoassay procedures.

The method of making these improved porous materials comprises the modification of the surfaces of porous substrates by a controlled deposition of plasma polymerizates on these surfaces from gas plasmas containing one or more polymerizable monomers, the gas plasmas being formed in a vacuum chamber by means of a glow discharge. Controlled deposition of the plasma polymerizates is achieved by control of the composite plasma parameter W/FM where W is the plasma excitation energy, F is the monomer flow rate and M is the average monomer molecular weight, the composite plasma parameter being controlled to an average level below $1.0 \times 10^9$ Joules per kilogram. In its most preferred embodiment, the method comprises a two step process wherein a surface of the porous substrate is first modified with a deposit of a plasma polymerizate, and then is further exposed to monomer in the absence of a glow. discharge so as to quench residual reactive sites in the plasma polymerizate deposit. Preferred monomers include amines and carboxylic acids, most particularly allylamine and acrylic acid. The controlled deposition of the plasma polymerizate onto the substrate surface results in improved porous membranes that exhibit reduced nonspecific binding behavior and increased signal-to-background ratios in analytical determinations. A particularly preferred embodiment involves a controlled deposition of a weakly acidic plasma polymerizate upon a positively charged porous substrate to provide improved porous membranes, which can thereby exhibit up to a ten-fold or higher improvement in signal-to-background ratios in chemiluminescent analyses of polynucleotides for specific submolecular nucleic acid sequences by oligonucleotide-containing probes.

The improved porous media attained by this method comprise porous substrates having deposited on at least one surface thereof a plasma polymerizate formed by exposure of the surface to a glow discharge gas plasma containing at least one monomer, whereby the modified surfaces of these porous substrates exhibit reduced nonspecific binding characteristics toward chemical probes in genomic and immunoassay analyses. The improved porous media of this invention are also characterized by increased ratios of signal-to-background or signal-to-noise (i.e., primarily, the ratio of specific binding versus nonspecific binding) in genomic and immunoassay analyses. In their preferred embodiment, these improved porous media comprise porous substrates having at least one surface modified by a deposit of a plasma polymerizate thereon, the plasma polymerizate being further modified by exposure to unreacted monomer whereby a majority of residual reactive sites in the plasma polymerizate are quenched. The preferred composition of the plasma polymerizate comprises a polymeric plasma reaction product derived from a glow discharge effected through a vapor of a monomer chosen from the group consisting of amines and carboxylic acids, most particularly allylamine or acrylic acid. The plasma polymerizate deposits are of sufficient thinness as not to significantly impede ingress of solvents and biomatter into surface pores, that is, surface porosity remains essentially unchanged overall. A particularly preferred composition comprises a cationically charged nylon porous substrate wherein the outermost surface has been coated with a thin layer of a weakly acidic plasma polymerizate.

These improved porous media provide advantages in reduced background and increased sensitivity in proteinaceous and genomic analyses wherein biopolymers are to be fixed onto a porous medium, and particularly where these biopolymers are then to be probed with one or more chemical probes specific to targeted submolecular sequences in those biopolymers. Furthermore, advantages are found in the use of such improved media in that lesser attention is required to the timing of photographic image development or color development, in that background build-up may be significantly or greatly diminished versus time. In chemiluminescent determinations, for example, image development may be allowed to proceed overnight, rather than having to be intercepted at a three, four or six hour period.

The method itself offers advantages in producing from a variety of porous substrates, that are otherwise deficient in background noise levels, improved porous media characterized by favorably-reduced background levels. The method itself offers also other advantages in providing improved porous media with retention of all or nearly all physical strength and handling characteristics normally associated with blotting membranes. Other features and advantages of the invention will be evident by means of the disclosure of the embodiments, to follow, or may become evident to one of ordinary skill in the art in the practice of the invention hereby disclosed.

DETAILED DESCRIPTION OF THE INVENTION

In accordance with the invention being disclosed herein, porous materials having reduced background and improved signal-to-noise properties in the analyses of proteinaceous and genomic biomatter are made by means of deposition of a plasma polymerizate on their surfaces from a glow discharge gas plasma. In a method of making these improved materials, a gas or a blend of gases is fed into an evacuated chamber, the gas or blend of gases is excited to a plasma state by a glow discharge maintained by application of energy in the form of an audiofrequency, a microwave frequency or a radiofrequency field, and a suitable substrate is exposed to the glow discharge gas plasma, whereby exposed surfaces of the substrate are modified by deposition of a plasma polymerizate.

Figure 1:
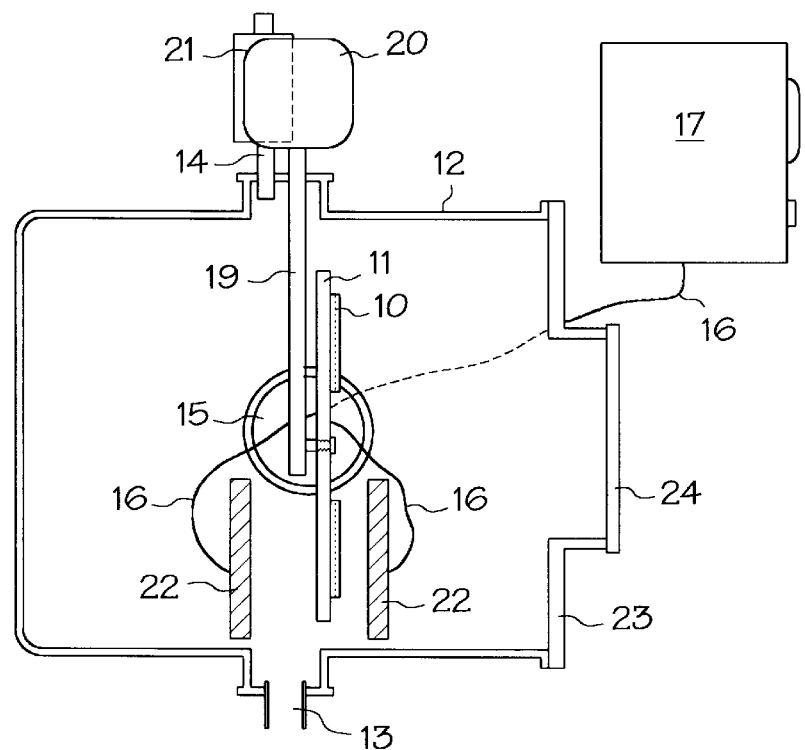
FIG. 1 is a schematic diagram of an apparatus used in the gas plasma modification of porous substrates.

FIG. 1 illustrates an apparatus in which the preparation of the improved porous media may be accomplished. A porous specimen 10 is conveniently mounted on a rotating disk 11 within a vacuum chamber 12 having connected thereto an outlet port 13 to a vacuum source, an inlet port 14 for introduction of the monomer vapor, and an electrical port 15 for introduction of an electrical cable 16 from a frequency signal generator 17. The rotating disk 11 is driven by a shaft 19 connected to a drive source such as a motor 20, shown here. The drive source 20 is preferably located externally to the vacuum chamber 12, with the drive shaft 19 penetrating a wall or port on the vacuum chamber via a mechanical seal. A monomer flow controller 21 is positioned at the monomer vapor inlet port 14, thereby to control the rate of monomer delivery to the vacuum chamber 12. One or a pair of electrodes 22, connected to the signal generator 17, is mounted either exteriorly to the vacuum chamber 12, or internally as shown in FIG. 1. An access plate 23, optionally containing a view port 24, provides a means of access into the vacuum chamber 12.

Figure 2:
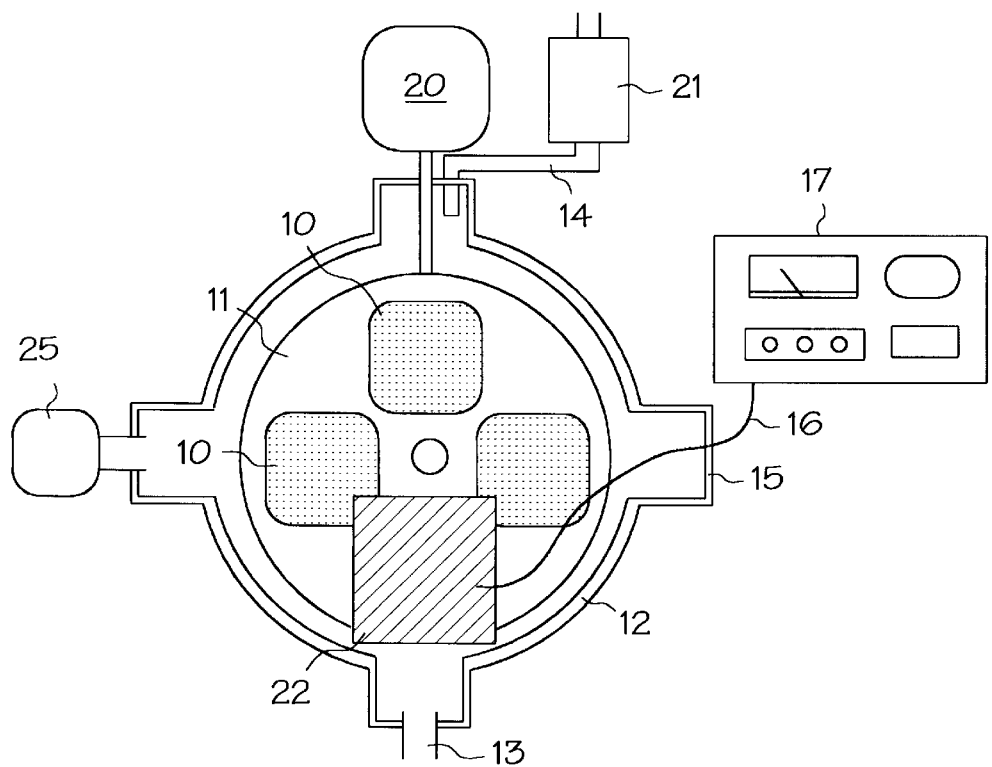
FIG. 2 is a another view of the same apparatus showing the mounting of porous material specimens.

FIG. 2 shows another view of the apparatus, as seen from the direction of the access plate 23. Specimens 10 of porous substrates are mounted on the rotating disk 11, which carries them between a pair of electrodes 22 (one shown) within the vacuum chamber 12. A pressure transducer 25 is also shown, mounted upon the vacuum chamber 12 by means of another port.

When a single electrode is utilized, the frequency signal is transmitted to this electrode. When a pair of electrodes is used, one is normally the signal transmitting electrode and the other is normally a ground electrode. Either or both electrodes are preferably positioned so that a glow discharge gas plasma is produced in a region within the vacuum chamber in which the specimen to be plasma-treated is either located or passed through. In the apparatus as shown, a pair of electrodes are positioned one on each side of a rotating disk, and specimens mounted on the disk are rotated through a glow discharge region located between the two electrodes. The walls of the vacuum apparatus preferably consist either of glass or metal, or combinations of glass and metallic parts. When a metal is used rather than glass, a view port is customarily placed in a wall of the vacuum chamber to allow for visual observation and confirmation of the presence of a glow discharge during plasma processing.

The rotational method of exposing specimens to a gas plasma between the electrodes provides a convenience in that more than one type of porous substrate may be exposed to essentially identical plasma treatment conditions for sake of comparison. Other apparatus designs and other means of bringing a porous substrate into contact with a gas plasma may be employed. Also, a continuous, uninterrupted exposure of a porous substrate to a gas plasma may also be employed for a time sufficient to modify the surface of the substrate with a suitable deposit of a plasma polymerizate. The particular design embodied in FIGS. 1 and 2 are not to be taken as a limiting in the practice of the invention. Variations in the design and operation of a gas plasma apparatus may be utilized, as would be evident to one of skill in the art. As an example, continuous sheeting of a porous substrate may be processed by roll-to-roll movement through a zone of gas plasma, within the scope of the invention, utilizing an apparatus designed for that purpose.

As an example of a method of making the improved porous materials for use in genomic or immunoassay analyses in accordance with the present invention, one or more specimens of porous substrates are mounted on the rotating disk, and the vacuum chamber is closed and evacuated to less than 1.0 mtorr, preferably to about 30 mtorr or less. Then, a monomer vapor is introduced into the vacuum chamber, usually on a continuous basis. Monomer vapor pressure is maintained at a preselected pressure level through control of the monomer inflow rate versus vacuum outflow rate. Rotation of the disk is started, and a glow discharge is initiated through the monomer vapor by means of a signal transmitted through the electrode pair. A plasma polymerizate forms on the surface or surfaces of the specimens, where these surfaces are exposed to the glow discharge gas plasma. The nature of the gas plasma is controlled according to the composite plasma parameter W/FM where W equals power input, F is the flow rate of the monomer vapor, and M is the molecular weight of the particular monomer selected for plasma polymerization. The nature of the plasma polymerizate that is deposited is in turn controlled by the composite plasma parameter, but also reflects the nature of the polymerizable monomer or monomers fed to the gas plasma. In addition to this parameter and to monomer selection, exposure time of the specimen to the gas plasma is preferably also controlled. Additional control may be exercised by generating an intermittent glow discharge such that plasma polymerizate deposited on a specimen's surface may have time to interact with monomer vapor in the absence of glow discharge, whereby some grafting of monomer may be effected. Additionally, the resulting plasma polymerizate may be exposed to unreacted monomer vapor in the absence of a glow discharge as a post-deposition treatment, whereby residual free radicals may be quenched.

Materials suitable for modification by the methods of this invention include porous sheet-like substrates composed of nitocelluloses, polyamides such as nylon 6 and nylon 66, polyolefins such as polyethylene or polypropylene, polysulfones, polyethersulfones, polyvinyl halides such as polyvinyl chloride, polyvinylidene halides such as polyvinylidene fluoride, polyfluorocarbons such as polytetrafluoroethylene, and even glass fiber felts. A variety of suitable porous substrates are commercially available in the form of porous blotting membranes. Examples of nitrocellulose membranes include Bio Trace NT (Gelman Sciences), Sartolon SM113 (Sartorius), and NitroBind (Micron Separations Inc). Examples of neutral nylon membranes include Biodyne A (Pall BioSupport Co), Hybond N (Amersham), Magna (Micron Separations Inc), and Sartolon SM200 (Sartorius). Examples of cationically charged nylon membranes include Biodyne B, Hybond N+, Magna Charge, and Sartolon SM203, made by the same set of companies. Many other such porous nylon substrates are commercially available from a variety of sources, as may be found in the publication *A Run on Nylons: A Survey of Nylon Blotting Membranes* (BioConsumer Review, February–March 1995, pp. 14–22). Examples of other charge-modified membranes include a polyethersulfone membrane (BioTrace HP, Gelman Sciences), and a polyvinylidene fluoride membrane (Immobilon-N, Millipore Corp). Porous membrane substrates may also be made such as disclosed in U.S. Pat. Nos. 4,340,479, 4,340,480, 4,450,126 and 4,247,498. The porous material need not necessarily be in a sheet-like form to be modified in accordance with this invention, but may exist in other dimensional shapes. Essentially, all blot membranes currently exist in a sheet-like form both for economies in manufacture and for practical handling in genomic and immunoassay analysis procedures.

Polymerizable monomers that may be used in the practice of the invention preferably comprise unsaturated organic compounds such as halogenated olefins, olefinic carboxylic acids and carboxylates, olefinic nitrile compounds, olefinic amines, oxygenated olefins and olefinic hydrocarbons. Such olefins include vinylic and allylic forms. The monomer need not be olefinic, however, to be polymerizable. Cyclic compounds such as cyclohexane, cyclopentane and cyclopropane are commonly polymerizable in gas plasmas by glow discharge methods. Derivatives of these cyclic compounds, such as 1,2-diaminocyclohexane for instance, are also commonly polymerizable in gas plasmas. Particularly preferred are polymerizable monomers containing hydroxyl, amino or carboxylic acid groups. Of these, particularly advantageous results have been obtained through use of allylamine or acrylic acid. Mixtures of polymerizable monomers may be used. Additionally, polymerizable monomers may be blended with other gases not generally considered as polymerizable in themselves, examples being argon, nitrogen and hydrogen. The polymerizable monomers are preferably introduced into the vacuum chamber in the form of a vapor. Polymerizable monomers having vapor pressures less than 0.01 torr are not generally suitable for use in the practice of this invention. Polymerizable monomers having vapor pressures of at least 0.05 torr at ambient room temperature are preferred. Where monomer grafting to plasma polymerizate deposits is employed, polymerizable monomers having vapor pressures of at least 1.0 torr at ambient conditions are particularly preferred.

The gas plasma pressure in the vacuum chamber may vary in the range of from 0.01 torr to 2.0 torr. Gas plasma pressures are preferably in the range of 0.05 to 1.0 torr for best results. To maintain desired pressure levels, especially since monomer is being consumed in the plasma polymerization operation, continuous inflow of monomer vapor to the plasma zone is normally practiced. When nonpolymerizable gases are blended with the monomer vapor, continuous removal of excess gases is accomplished by simultaneously pumping through the vacuum port to a vacuum source. Since some nonpolymerizable gases are often evolved from glow discharge gas plasmas, it is advantageous to control gas plasma pressure at least in part through simultaneous vacuum pumping during plasma polymerizate deposition on a substrate in the process of this invention.

The glow discharge through the gas or blend of gases in the vacuum chamber may be initiated by means of an audiofrequency, a microwave frequency or a radiofrequency field transmitted to or through a zone in the vacuum chamber. Particularly preferred is the use of a radiofrequency (RF) discharge, transmitted through a spatial zone in the vacuum chamber by an electrode connected to an RF signal generator. A more localized and intensified gas plasma is attained by means of an electrode pair, whereas a more diffuse gas plasma is a result of a single electrode. A rather broad range of RF signal frequencies starting as low as 50 kHz may be used in causing and maintaining a glow discharge through the monomer vapor. The 50 kHz frequency was used with good effect in the experimental examples given at the end of this disclosure. In commercial scale usage of RF plasma polymerization, an assigned radiofrequency of 13.56 MHz may be more preferable to use to avoid potential radio interference problems.

The glow discharge need not be continuous, but may be intermittent in nature during plasma polymerizate deposition. Or, a continuous glow discharge may be employed, but exposure of a substrate surface to the gas plasma may be intermittent during the overall polymerizate deposition process. Or, both a continuous glow discharge and a continuous exposure of a substrate surface to the resulting gas plasma for a desired overall deposition time may be employed. The plasma polymerizate that deposits onto the porous substrate generally will not have the same elemental composition as the incoming polymerizable monomer (or monomers). During the plasma polymerization, some fragmentation and loss of specific elements or elemental groups naturally occurs. Thus, in the plasma polymerization of allylamine, nitrogen content of the plasma polymerizate is typically lower than would correspond to pure polyallylamine. Similarly, in the plasma polymerization of acrylic acid, carboxyl content of the plasma polymerizate is typically lower than would correspond to pure polyacrylic acid. Exposure time to either of these unreacted monomers in the absence of a gas plasma, as through intermittent exposure to a glow discharge, allows for grafting of the monomer to the plasma polymerizate, thereby increasing somewhat the level of the functional group (amine or carboxylic acid) in the final deposit. Time intervals between plasma exposure and grafting exposure can be varied from a fraction of a second to several minutes, using for example the rotational method illustrated in FIG. 1 and FIG. 2.

Figure 3:
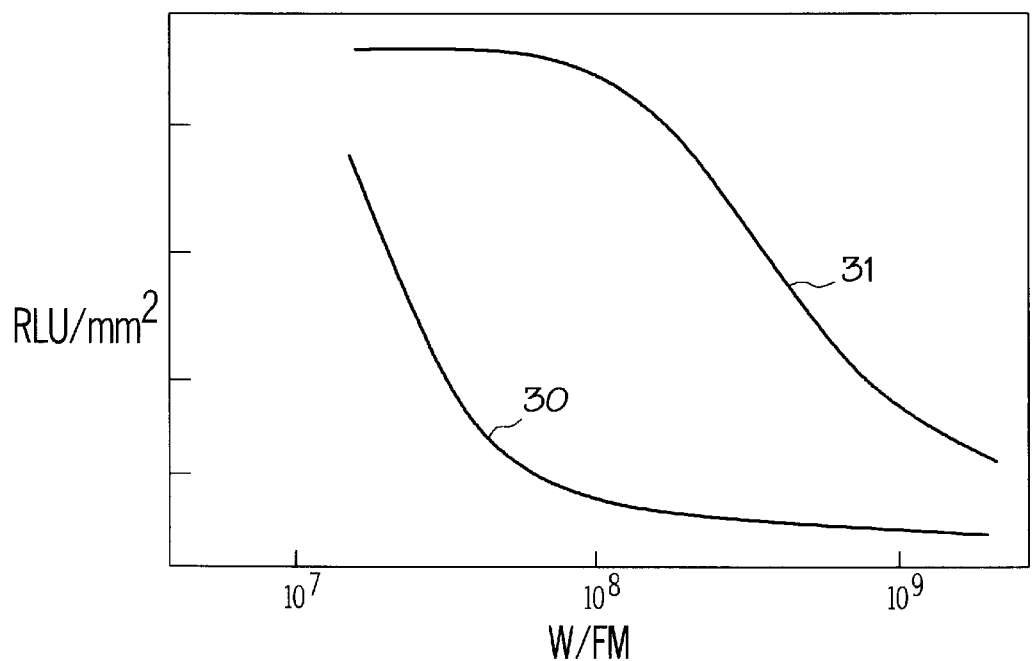
FIG. 3 is a graph illustrating a generalized effect of the composite plasma parameter on signal intensity and background noise.
Figure 4:
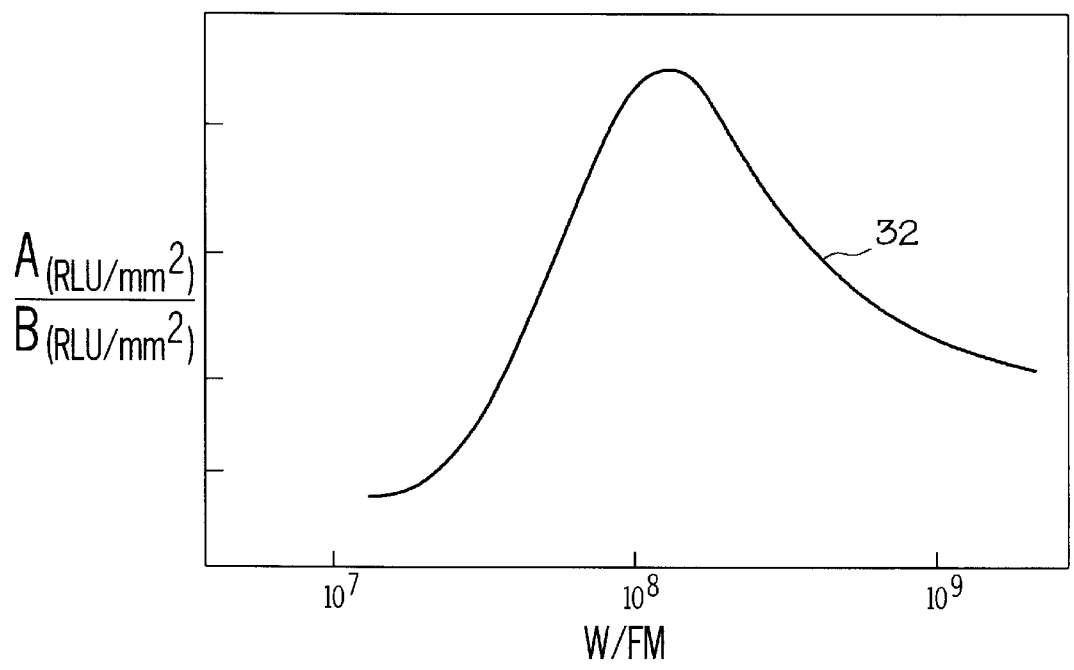
FIG. 4 is a graph illustrating signal-to-background ratio as a generalized function of the composite plasma parameter.

As stated earlier, the deposition of the plasma polymerizate is controlled by control of the composite plasma parameter W/FM where W is the plasma excitation energy, F is the monomer flow rate and M is the average monomer molecular weight. Referring to FIG. 3, it has been observed in chemiluminescent determinations of genomic sequences that the intensities of the background and of the signal vary differentially in response to the composite plasma parameter that is employed in the deposition of the plasma polymerizate. This is illustrated in a general relationship in FIG. 3 where light intensity in RLU/mm$^2$ is plotted against W/FM, wherein background noise, represented by the lower curve 30, decreases more rapidly as a function of increasing W/FM than does signal intensity, represented by the upper curve 31. Referring to FIG. 4, the ratio of signal intensity over background intensity, i.e., 30/31, when plotted as a function of increasing W/FM, correspondingly passes through a maximum as illustrated by the curve 32. To attain improved signal to background levels as depicted in FIG. 4, the composite plasma parameter is preferably controlled to an average level below $1.0 \times 10^9$ Joules per kilogram. A preferred range for the composite plasma parameter is from about $0.5 \times 10^8$ J/kg up to about $1.0 \times 10^9$ J/kg. It has been found that a particularly preferred range for this parameter is from about 2.0 to about $7.0 \times 10^8$ J/kg for monomers such as allylamine and acrylic acid, which range corresponds generally to the apical region of the curve 32.

The exposure time for a porous substrate to the glow discharge gas plasma may be varied from as little as 0.25 minute to as long as 30 minutes. The optimum time of exposure may be expected to vary as an inverse function of the magnitude of the composite plasma parameter, i.e., at the low end of the composite plasma parameter range (about $0.5 \times 10^8$ J/kg), a longer time of exposure would be applicable. At the high end of the composite plasma parameter range (about $1.0 \times 10^9$ J/kg), a shorter time of exposure would be applicable. At a composite plasma parameter level within the particularly preferred range of 2.0 to about $7.0 \times 10^8$ J/kg, plasma exposure times of 0.4 minute to 4.0 minutes have been found to be particularly preferred.

In addition to exposure time to the gas plasma, during which plasma polymerizate is deposited on exposed surfaces of the porous substrate, subsequent exposure to unreacted monomer in the absence of a gas plasma is often preferred. A freshly deposited plasma polymerizate normally contains a significant number of reactive sites such as strained linkages, residual free radicals, and other types of unsatisfied valences. These sites typically bind oxygen when exposed to air, leading to some oxidation of the plasma polymerizate. These sites represent a source of some potential instability in the composition, shelf stability and behavioral characteristics of the plasma polymerizate. It is desirable to produce in accordance with the present invention modified porous substrates wherein the physical and chemical attributes are generally stable. It is a preferred option, therefore, to subsequently expose the plasma polymerizate to a vapor of a monomer to quench residual reactive sites that would otherwise oxidize in air. This monomer may be a polymerizable monomer as used in the plasma polymerization. Or it may be a terminating monomer that simply binds to a residual reactive site and eliminates its reactivity toward oxygen. Terminating monomers may include, for example, organic amines, mercaptans and olefins. It has been found in the practice of the present invention that a polymerizable monomer as used in the plasma polymerization step is preferably also used as a post-deposition quenching monomer. An effect of using the same polymerizable monomer throughout is to maximize the population of any functional group associated with the specific polymerizable monomer. For example, if the polymerizable monomer is acrylic acid, and carboxylic functional groups are desired in the plasma polymerizate, quenching of the deposited plasma polymerizate with additional acrylic acid monomer vapor will result in attachment of additional carboxylic groups.

The quenching treatment may be conducted at an elevated pressure of the vapor of a monomer. Thus, for example, a gas plasma pressure of 100 mtorr may be used in the modification of a porous substrate with a plasma polymerizate, followed by quenching of the plasma polymerizate with a vapor of a monomer at 1.0 torr or higher. The range of pressure at which the modified porous substrate is exposed to the quenching monomer may vary from the original pressure of the gas plasma to a pressure in excess of atmospheric pressure. The upper range of monomer pressure will be normally limited, however, by the ambient vapor pressure of said monomer as an upper limit. The range of quenching time in monomer vapor at elevated monomer pressure may be varied from one minute to one week, or even longer. It is preferable, however, to operate at an exposure time and monomer pressure level to attain a desirable level of quenching within a period of one minute to one hour. For example, at a monomer pressure of 1.0 torr, a quenching exposure time of 30 minutes has been found to give good results.

The improved porous media of the invention consist of porous substrates having a plasma polymerizate deposited on at least one surface thereof from a gas plasma containing one or more polymerizable monomers, these modified surfaces now having a biopolymer binding characteristic that is altered by the plasma polymerizate deposit. More specifically in the case of genomic material, the originally unmodified surfaces possessed an initial ratio of nucleic acid biopolymer (e.g., DNA, RNA) binding versus nonspecific binding of an oligonucleotide probe, whereas the surfaces modified with plasma polymerizate deposited in accordance with the method of this invention exhibit a second ratio of nucleic acid biopolymer (e.g., DNA, RNA) binding versus nonspecific binding of the oligonucleotide probe, the second ratio being higher. And whereas the unmodified surfaces of these porous substrates had a first signal-to-background ratio in a chemiluminescence determination of, for example, a specific DNA or RNA sequence by means of a DNA or RNA probe, the surfaces modified with plasma polymerizate deposits in accordance with the method of this invention exhibit a second signal-to-background ratio in a chemiluminescence determination of the DNA or RNA sequence by means of the oligonucleotide probe, the second ratio being higher.

These improved porous media are marked by the presence of the plasma polymerizate on at least one of their surfaces, wherein an ultrathin, contiguous, adherent layer of the plasma polymerizate coats exposed superficial portions of the media surfaces. Where either surface of the initial porous substrate may be used as the receiving surface for a biopolymer in a genomic or immunoassay analysis, either or both surfaces may be coated with the plasma polymerizate to attain an improved blotting medium in accordance with the present invention. Where the initial porous substrate has a singularly preferred surface intended to receive the biopolymer in a genomic or immunoassay analysis, this same surface is preferably the surface coated with the plasma polymerizate in accordance with this invention. The plasma polymerizate may be present at a deposit thickness in the range of 100 to 5,000 Angstroms, more preferably 100 to 2,000 Angstroms, at the outer most projections of the exposed surface. Some presence of plasma polymerizate on the walls of surface pores within the surface layers of the porous substrates may be anticipated, but this presence will generally be limited to about one micrometer in surface depth, more probably to about 0.1 micrometer or less in surface depth, with thickness of the coating decreasing with increasing depth into the surface layer of the porous substrate.

Sizes of pores in the surfaces of the porous substrates may be varied widely, both as a function of substrate chemical composition and as a function of substrate manufacturing methods. In the case of most polymeric porous substrates of the microfiltration type, these pores will be in the range of 0.1 to 2 micrometer average diameter. The coating thickness of the plasma polymerizate is preferably of sufficient thinness as not to restrict the average diameter of the surface pores as would be observable via scanning electron microscopy. Restriction of membrane pore size is believed to be neither a requirement nor a significant factor in the modification of the porous substrates to obtain the improved porous media of the invention. In their most preferred embodiment, these improved porous media will retain fluid transport rates that are essentially equivalent with initial rates characteristic of the unmodified porous substrates.

A particularly preferred embodiment of an improved porous medium made in accordance with this invention comprises a positively charged porous substrate having a thin layer of a weakly anionic layer af plasma polymerizate deposited upon at least one of its surfaces. Thus, a cationically charged porous substrate, particularly a porous nylon membrane, has the outermost region of at least one of its surfaces coated with a plasma polymerizate formed from a glow discharge gas plasma containing a carboxylic acid monomer, or is subsequently exposed in the absence of a glow discharge to such a monomer for purpose of grafting the monomer onto the plasma polymerizate. The same monomer may be incorporated in both the plasma polymerization and the grafting stages. A particularly preferred monomer for this purpose is acrylic acid, and the resulting plasma polymerizate has carboxylic groups in its chemical composition.

The following experimental examples are given to further illustrate the methods and products of the invention.

EXAMPLE 1

A positively charged, porous nylon blotting membrane (Sartolon SM203, Sartorius) was modified by the plasma polymerization of acrylic acid onto one of its surfaces. A specimen of the nylon membrane was attached to a rotatable disk within a bell jar plasma reactor containing two parallel electrodes inside the chamber, generally as illustrated in FIG. 1. The bell jar was evacuated, then maintained at a pressure of about 98 mtorr with acrylic acid vapor. Monomer flow rate was 2 sccm (standard cubic centimeter per minute). Plasma excitation power was 50 watts, using RF at 50 kHz. The disk supporting the specimen was rotated for 5 minutes at about 10 rpm through a glow discharge plasma of the monomer, and direct plasma exposure time was calculated to be 2 minutes. Grafting of the monomer to freshly deposited plasma polymerizate during rotation out of the immediate region of the glow discharge was allowed. A quenching process was followed thereafter, whereby the specimen was exposed to unreacted acrylic acid monomer in the absence of a glow discharge at a vapor pressure above 1 torr for 30 minutes. The specimen was then removed from the apparatus.

Duplicate samples sized of 9 mm×13 mm were cut from the coated specimen and were prepared for chemiluminescence slot blot analytical procedure. The samples were wetted with sterile water and mounted in a slot blot apparatus. Then 25 µl of diluted DNA solution containing 200 attomols/ml of a pGem®-luc DNA digest (PGEM® is a trademark of Promega Corp., Madison, Wis.) were added to each well of the slot blot apparatus. A partial vacuum was applied to draw the DNA solution onto the sample. The sample membranes were removed from apparatus and hybridized with 1 ml of 150 femtomoles of an oligonucleotide-alkaline phosphatase (LIGHTSMITH™ Probe 2, Promega Corp.). After washing in 1×SSC (sodium citrate buffer), followed by a single wash in a solution of 100 mmole diethanolamine and 10 mmoles $MgCl_2$ (pH 10), membrane samples were divided into the slot bands (3 $mm^2$) for signal intensity determinations and remainder portions (114 $mm^2$) for background intensity determinations These were placed singly in 12×75 mm borosilicate glass tubes for chemiluminescent analysis. With 250 µl of chemiluminescent substrate (Quantum Yield Substrate, AMPPDI, Promega Corp.) added to the test tubes, the tubes were placed in a luminometer, and relative light units (RLU) were counted for 30 seconds. Unmodified controls were run alongside the plasma-modified samples through the chemiluminescence analysis. The plasma-modified samples exhibited averaged readings of 759,277 $RLU/mm^2$ from the slot band and 5,441 $RLU/mm^2$ from the surrounding background. Equivalent measurements for the controls were 1,305,473 and 41,100 $RLU/mm^2$ respectively. Signal-to-background (signal-to-noise) ratio for the plasma-modified samples was 140, compared to a signal-to-noise ratio of only 32 for the untreated controls. The modified membrane thus achieved a 4-fold increase in sensitivity over the unmodified porous nylon substrate.

EXAMPLE 2

In the same apparatus and manner as in Example 1, a porous polyvinylidene fluoride membrane (Immobilon-N, Millipore Corp.) was modified by surface deposition of a plasma polymerizate of allylamine. Monomer flow rate was 2 sccm. Plasma excitation power was 50 watts. Plasma exposure time was 3.6 minutes at about 93 mtorr plasma gas pressure. Quenching of the samples was subsequently performed by exposure to allylamine monomer in the absence of a glow discharge at a monomer vapor pressure above 1 torr for 30 minutes. Chemiluminescence analyses were done as in example 1, including unmodified controls alongside the plasma-modified samples. The plasma-modified samples exhibited 167,224 $RLU/mm^2$ from the slot band and 6,149 $RLU/mm^2$ from the surrounding background. Equivalent measurements for the controls were 146,573 and 63,978 $RLU/mm^2$ respectively. Signal-to-background (signal-to-noise) ratio for the plasma-modified sample was 27, compared to a signal-to-noise ratio of only 2.3 for the untreated control. The modified membrane thus achieved nearly a 12-fold increase in sensitivity over the unmodified porous polyvinylidene fluoride substrate.

EXAMPLES 3–5

In the same apparatus and general procedure of Example 1, porous, positively charged nylon membranes (Biodyne B, Pall Corp.) were modified with acrylic acid plasma polymerizates. In example 3, plasma excitation power (W) was 25 watts, monomer flow rate (F) was 2.1 sccm, and acrylic acid monomer molecular weight (M) was taken to be 72 g/mole, giving a composite plasma parameter of $2.22 \times 10^8$ J/kg. For example 4, W was 50 watts and F was 1.7 sccm, leading to a composite plasma parameter of $5.49 \times 10^8$ J/kg. In example 5, W was 50 watts and F was 0.4 sccm, leading to a composite plasma parameter of $2.33 \times 10^8$ J/kg. Plasma exposure time was 2 minutes. The post-deposition quenching treatment process was followed, with samples being exposed to unreacted acrylic acid monomer at a gas pressure above 1 torr for 30 min. Plasma-modified membranes of these three examples were compared to unmodified controls in a chemiluminescence procedure.

A dot blot method with pRNasin 26-mer alkaline phosphatase oligonucleotide conjugate as a DNA probe was used to measure reductions of background noise and improvements in signal-to-noise ratios resulting from plasma modification. A target polynucleotide (pRNasin plasmids) was diluted to a final concentration of 500 attomoles/µl in 0.4M NaOH. After denaturing, two-fold serial dilution's of the target DNA in 0.4 M NaOH generated a dilution series ranging from 500 to 0.5 attomoles/µl. A 1 µl of each of the dilution's directly spotted onto each of the membranes and fixed in place. Half of these samples were treated with a blocking solution. Target DNA in all these samples was then hybridized with 1 ml of 150 fmoles of oligonucleotide-alkaline phosphatase ( LIGHTSMITH™ oligo-AP Probe). After washing in 1×SSC, followed by single wash in a solution of 100 mmole diethanolamine and 1 mmoles $MgCl_2$ (pH 10), membrane samples were placed in singly in 12×75 mm borosilicate glass tubes and analyzed by chemiluminescent techniques. With 250 µl of chemiluminescent substrate (Quantum Yield Substrate, AMPPDI added, the membrane samples were placed in a luminometer and relative light units were counted for 30 seconds. Chemiluminescence measurements were carried out independently for the dot blots and backgrounds. The dot blots had been carefully cut out by punch tool (5 mm diameter) and compared with the remainder (background). Results were as shown in Table I. In all three conditions of plasma polymerizate deposition, the plasma-modified membranes showed much lower background noise than the control. At a medium plasma composite parameter W/FM of $5.49 \times 10^8$ J/kg, the lowest background noise (0.8% of control) and the highest signal-to-noise ratio (7.44) were obtained.

TABLE I

| Sample | Signal (A) Chemiluminescence Light Density of Dot Blot (RLU at 125 attomoles) | Noise (B) Chemiluminescence Light Density of Background (RLU at 125 attomoles) | Signal to Noise Ratio (A)/(B) |
|---|---|---|---|
| Control | 1,211,112 | 1,132,515 | 1.07 |
| Control with Blocking | 398,406 | 355,014 | 1.12 |
| Example 3 | 325,340 | 297,676 | 1.09 |
| Example 4 | 64,102 | 8,611 | 7.44 |
| Example 5 | 232,138 | 189,472 | 1.23 |

EXAMPLES 6 AND 7

Positively charged nylon membranes (MagnaCharge, Micron Separation Inc.) were modified under approximately the same conditions as in examples 3–5. Monomer used in the modification was acrylic acid and plasma exposure time was 2 minutes. In example 6, W was 25 watts, F was 2.1 sccm, and the composite plasma parameter was $2.22 \times 10^8$ J/kg. In example 7, W was 50 watts, F was 1.7 sccm, and the composite plasma parameter was $5.49 \times 10^8$ J/kg. The quenching treatment process was followed, with samples being exposed to unreacted acrylic acid monomer at the gas pressure above 1 torr for 30 min. A dot blot method with pRNasin 26-mer alkaline phosphatase oligonucleotide conjugate as a DNA probe was used to evaluate the effect of plasma modification on background noise and signal-to-noise ratio. Chemiluminescence detection procedures are same as in examples 3–5. Results are shown in Table II. The modified membranes exhibited lower background noise than the controls. At a medium plasma composite parameter W/FM of $5.49 \times 10^8$ J/kg, the lowest background noise (3.0% of control) and the highest signal-to-noise ration of 5.52 were observed.

TABLE II

| Sample | Signal (A) Chemiluminescence Light Density of Dot Blot (RLU at 125 attomoles) | Noise (B) Chemiluminescence Light Density of Background (RLU at 125 attomoles) | Signal to Noise Ratio (A)/(B) |
|---|---|---|---|
| Control | 109,280 | 86,807 | 1.26 |
| Control with Blocking | 57,012 | 52,492 | 1.09 |
| Example 6 | 76,339 | 59,063 | 1.29 |
| Example 7 | 14,262 | 2,582 | 5.52 |

EXAMPLES 8–10

Porous, positively charged nylon membranes (Biodyne B, Pall Corp.) were modified by plasma deposition of a polymerizate from an acrylic acid gas plasma by the same technique as in example 1. Plasma composite parameter W/FM was $4.67 \times 10^8$ J/kg. Plasma exposure times were varied from zero to 2.0 minutes, followed by quenching exposure to unreacted acrylic acid monomer at a gas pressure above 1 torr for 30 min. Chemiluminescence tests were run using the pRNasin method as in example 2, and results are shown in Table III as a function of plasma exposure time. Background noise decreased and signal to noise ratio increased with increasing time of plasma exposure. At 2.0 minutes of plasma exposure time, the signal-to-noise ratio was 7.44.

TABLE III

| Sample | Plasma Exposure Time (min) | Signal (A) Chemiluminescence Light Density of Dot Blot (RLU at 125 attomoles) | Noise (B) Chemiluminescence Light Density of Background (RLU at 125 attomoles) | Signal to Noise Ratio (A)/(B) |
|---|---|---|---|---|
| Control | 0 | 1,211,112 | 1,132,515 | 1.07 |
| Control with blocking | 0 | 398,406 | 355,014 | 1.12 |
| Example 8 | 0.4 | 205,600 | 173,359 | 1.19 |
| Example 9 | 1.0 | 199,882 | 106,565 | 1.88 |
| Example 10 | 2.0 | 64,102 | 8,611 | 7.44 |

EXAMPLES 11–13

Additional samples of Biodyne nylon membranes were modified as in Examples 8–10, but at a composite plasma parameter of $2.33 \times 10^8$ J/kg. Plasma exposure times were varied from zero to 4.0 minutes. Chemiluminescence tests were run using the pRNasin method as in example 2. Results are shown in Table IV. Background noise was reduced generally with increasing time of the plasma exposure. For the samples corresponding to 3.0 minutes of plasma exposure, the signal-to-noise ratio reached a maximum value of 1.64.

TABLE IV

| Sample | Plasma Exposure Time (min) | Signal (A) Chemiluminescence Light Density of Dot Blot (RLU at 125 attomoles) | Noise (B) Chemiluminescence Light Density of Background (RLU at 125 attomoles) | Signal to Noise Ratio (A)/(B) |
|---|---|---|---|---|
| Control | 0 | 1,211,112 | 1,132,515 | 1.07 |
| Control with Blocking | 0 | 398,406 | 355,014 | 1.12 |
| Example 11 | 2.0 | 325,340 | 297,676 | 1.09 |
| Example 12 | 3.0 | 144,938 | 88,491 | 1.64 |
| Example 13 | 4.0 | 25,423 | 21,093 | 1.21 |

EXAMPLES 14–16

Nylon membranes (MagnaCharge, Micron Separation Inc., positively charged) were modified by the same plasma technique as in example 1. The monomer was acrylic acid. The plasma composite parameter W/FM was $2.33 \times 10^8$ J/kg. Plasma exposure times were varied. Samples were exposed after plasma treatment to unreacted monomer at the gas pressure above 1 torr for 30 min. Chemiluminescence tests were run using the pRNasin method as in example 2. Results are shown in Table V. Background noise was reduced with the increase of the plasma exposure time. At 3.0 minutes plasma exposure time, the background noise was 13.7% of the control and the value of signal-to-noise ratio reached a maximum of 4.68.

TABLE V

| Sample | Plasma Exposure Time (min) | Signal (A) Chemiluminescence Light Density of Dot Blot (RLU at 125 attomoles) | Noise (B) Chemiluminescence Light Density of Background (RLU at 125 attomoles) | Signal to Noise Ratio (A)/(B) |
|---|---|---|---|---|
| Control | 0 | 109,280 | 86,807 | 1.26 |
| Control with Blocking | 0 | 57,012 | 52,492 | 1.09 |
| Example 14 | 2.0 | 76,339 | 59,063 | 1.29 |
| Example 15 | 3.0 | 55,670 | 11,898 | 4.68 |
| Example 16 | 4.0 | 8,877 | 7,093 | 1.25 |

EXAMPLES 17

Nylon membranes (Biodyne B, Pall Corp., positively charged) were modified by the plasma technique (Example 10). Monomer used for the modification was acrylic acid (molecular weight: 72 g/mole). Plasma excitation power was 50 watts, monomer flow rate was 2 sccm and Plasma composite parameter W/FM was $4.67 \times 10^8$ J/kg. Plasma exposure time was 1 minute. Grafting process was followed and samples were exposed to unreacted monomer at the gas pressure above 1 torr for 30 min. A chemiluminescence dot blot analysis was run using three serial dilutions of a target DNA followed by hybridization with the pRNasin probe. Results are shown in Table VI. Data regression analysis was applied in the relation between logarithm of DNA target concentration and chemiluminescence light density. Modified membrane exhibited 1.7 times higher sensitivity with 3.7% of background noise level of control. The coefficient of determination of example 17 was 0.965 and showed greater linearity over control (0.825) and control with blocking (0.060).

TABLE VI

| DNA Target Concentration (attomoles) | Chemiluminescence Light Density of Dot Blot (RLU) | | |
|---|---|---|---|
| | Control | Control with Blocking | Example 18 |
| 125 | 1,211,112 | 398,406 | 199,882 |
| 31.3 | 1,164,130 | 448,799 | 141,193 |
| 7.7 | 1,158,616 | 381,446 | 111,017 |
| Background | 1,132,515 | 355,014 | 106,565 |
| Data Regression Analysis (X; log (DNA Concentration), Y; Light Density (RLU)) | | | |
| Slope | 43,297 | 14,217 | 73,366 |
| Y-Intercept | 1,113,311 | 48,025 | 41,163 |
| R Squared* | 0.825 | 0.060 | 0.965 |

*The coefficient of determination

EXAMPLES 18

Nylon membranes (MagnaCharge, Micron Separations Inc., positively charged) were modified by the plasma conditions of example 16. The monomer was acrylic acid (M=72 g/mole), plasma excitation power was 25 watts, monomer flow rate was 2 sccm, and plasma composite parameter W/FM was $2.33 \times 10^8$ J/kg. Plasma exposure time was 3 minutes. Samples were exposed to unreacted monomer at the gas pressure above 1 torr for 30 min after plasma polymerizate deposition. Results are shown in Table VII. Modified membrane exhibited 1.35 times higher sensitivity with 22.5% of ground noise level of control. The coefficient of determination of Example 18 was 0.994 and showed greater linearity over 0.825 control (0.939) and control with blocking (0.914).

TABLE VII

| DNA Target Concentration (attomoles) | Chemiluminescence Light Density of Dot Blot (RLU) | | |
|---|---|---|---|
| | Control | Control with Blocking | Example 19 |
| 125 | 109,280 | 57,012 | 55,670 |
| 31.3 | 97,650 | 56,417 | 46,263 |
| 7.7 | 93,074 | 54,444 | 33,816 |
| Background | 86,807 | 52,492 | 11,896 |
| Data Regression Analysis (X; log (DNA Concentration), Y; Light Density (RLU)) | | | |
| Slope | 13,376 | 2,123 | 18,059 |
| Y-Intercept | 80,030 | 52,786 | 18,286 |
| R Squared* | 0.939 | 0.914 | 0.994 |

*The coefficient of determination

We claim:

1. A method of analysis of proteinaceous and genomic biopolymers comprising:
   adhering a biopolymer onto a surface of a porous substrate having a plasma polymerizate deposited on said surface from a gas plasma containing at least one polymerizable monomer therein;
   probing the biopolymer with at least one chemical probe for a specific submolecular sequence in the biopolymer, the presence of said submolecular sequence being detectable by means of a specific binding of said probe to said submolecular sequence; and measuring the presence of said probe through chemiluminescence, fluorescence, radiography, or color development;
   wherein said surface of the porous substrate without said plasma polymerizate has a first ratio of specific binding of said probe to said submolecular sequence in the biopolymer versus nonspecific binding of said probe to the porous substrate, the plasma polymerizate deposited upon said surface of the porous substrate causing said surface to exhibit a second ratio of specific versus nonspecific binding of the said probe, the second ratio being higher.

2. The method according to claim 1 wherein said surface of the porous substrate has a first ratio of binding of a polynucleotide versus nonspecific binding of an oligonucleotide-containing probe for the polynucleotide resulting in a first signal-to-background ratio in an analytical determination of a nucleic acid sequence in the polynucleotide by means of the oligonucleotide-containing probe, the plasma polymerizate deposited upon said surface of the porous substrate causing said surface to exhibit a second ratio of binding of the polynucleotide versus nonspecific binding of the oligonucleotide-containing probe, resulting in a second signal-to-background ratio in said determination, the second signal-to-background ratio being higher.

3. The method according to claim 2 wherein at least one polymerizable monomer is chosen from the group consisting of an amine and a carboxylic acid.

4. The method according to claim 3 wherein the monomer is allylamine.

5. The method according to claim 3 wherein the monomer is acrylic acid.

6. The method according to claim 1 wherein at least one polymerizable monomer is chosen from the group consisting of an amine and a carboxylic acid.

7. The method according to claim 6 wherein the monomer is allylamine.

8. The method according to claim 6 wherein the monomer is acrylic acid.

9. An article useful in analyses of proteinaceous or genomic biopolymers, comprising a porous sheet having at least one surface thereof suitable to receive a biopolymer in a blot analysis, said surface having an initial level of binding capacity for the biopolymer and an initial nonspecific binding level for a chemical probe to be used in an analysis of the biopolymer, said surface having deposited thereon a plasma polymerizate from a gas plasma containing a first monomer therein, said plasma polymerizate having been exposed to a vapor comprising a second monomer in the absence of a glow discharge subsequent to its being deposited on the porous sheet, the plasma polymerizate containing residual free radicals, the second monomer quenching the residual free radicals, causing said surface to exhibit a reduced nonspecific binding level for the chemical probe.

10. The article according to claim 9 wherein the second monomer is selected from a group consisting of an amine and a carboxylic acid.

11. The article according to claim 9 wherein the second monomer is identical with the first monomer.

12. An article useful in genomic analyses comprising a cationically charged, porous, substrate comprising a nylon having a deposit on at least one surface thereof, said deposit comprising a plasma polymerizate containing a plurality of acidic groups, said plasma polymerizate, subsequent to its being deposited on the porous substrate, having been exposed to a vapor comprising a polymerizable monomer in the absence of a glow discharge, a portion of the polymerizable monomer being grafted onto the plasma polymerizate, said surface having an initial level of binding capacity for a polynucleotide target molecule and an initial nonspecific binding level for an oligonucleotide-containing probe to be used in an analysis of the polynucleotide target molecule, said plasma polymerizate causing said surface to exhibit a reduced nonspecific binding level for the oligonucleotide-containing probe.

13. The article according to claim 12 wherein the polymerizable monomer contains a carboxylic acid group.

14. A method of making an improved material for analysis of biopolymers via blot analysis techniques, comprising:

a) providing a gas comprising a vapor of a first monomer within a vacuum chamber, b) exciting said gas to a plasma state by means of a glow discharge, c) exposing a surface of a porous substrate, having a first level of nonspecific binding of a chemical probe, to the gas plasma for a time sufficient to deposit a plasma polymerizate upon the exposed surface, said plasma polymerizate containing residual free radicals, d) exposing the plasma polymerizate to a vapor of a second monomer in the absence of a glow discharge for a time sufficient to quench a majority of the residual free radicals, and e) removing the porous substrate from the vacuum chamber, wherein the surface of the porous substrate is thereby modified to provide a reduced level of nonspecific binding of the chemical probe in a subsequent blot analysis of a biopolymer.

15. The method according to claim 14 wherein the first monomer is chosen from a group consisting of an amine and a carboxylic acid.

16. The method according to claim 14 wherein the plasma polymerizate is exposed to the second monomer at a pressure of at least 1.0 torr.

17. The method according to claim 16 wherein the second monomer is identical to the first monomer.

18. A method of making an improved porous substrate for genomic analysis comprising modifying at least one surface of a porous substrate by a controlled deposition of a plasma polymerizate upon the surface, said surface of the porous substrate having a first ratio of binding of a biopolymer versus nonspecific binding of a chemical probe for the biopolymer in a blot analysis, the plasma polymerizate causing an increased ratio of binding of the biopolymer versus nonspecific binding of the chemical probe by the thus-modified surface, the controlled deposition of the plasma polymerizate comprising an exposure of the surface of the porous substrate to a gas plasma containing a first monomer at a plasma composite parameter W/FM of less than $1.0 \times 10^9$ Joules per kilogram for a time less than 30 minutes, said plasma polymerizate after deposition being further exposed to a vapor of a second monomer in the absence of a glow discharge.

19. The method according to claim 18 wherein the vapor of the second monomer is at a pressure of at least 1.0 torr.

20. The method according to claim 19 wherein the second monomer is identical to the first monomer.

21. A method of analysis of a proteinaceous or genomic biopolymer comprising adhering a biopolymer onto a surface of a porous substrate, then probing the biopolymer with at least one chemical probe for a specific submolecular sequence in the biopolymer, the presence of the specific submolecular sequence being detectable by means of a specific binding of the chemical probe to the specific submolecular sequence in the biopolymer, the surface of the porous substrate having a reduced level of nonspecific binding of the chemical probe by reason of a deposit of a plasma polymerizate on said surface.

22. The method according to claim 21 wherein the presence of the specific submolecular sequence is determinable through use of a nonradioactive probe.

23. The method according to claim 22 wherein the presence of the specific submolecular sequence is determinable through chemiluminescence, fluorescence or color development.

24. The method according to claim 21 wherein a signal-to-background ratio of specific versus nonspecific binding of the chemical probe is increased for said surface due to the presence of the plasma polymerizate deposited on said surface.

* * * * *